United States Patent [19]

Hirai et al.

[11] 4,170,708

[45] Oct. 9, 1979

[54] PROCESS FOR PREPARING AROMATIC URETHANES

[75] Inventors: Yutaka Hirai; Katsuharu Miyata; Seiji Hasegawa, all of Omuta, Japan

[73] Assignee: Mitsui Toatsu Chemicals, Incorporated, Tokyo, Japan

[21] Appl. No.: 664,995

[22] Filed: Mar. 8, 1976

[30] Foreign Application Priority Data

Apr. 2, 1975 [JP] Japan ................................. 50/39119

[51] Int. Cl.² ........................................ C07C 125/06
[52] U.S. Cl. .............................. 560/24; 260/239 BE;
260/346.3; 544/37; 560/9; 560/13; 560/14;
560/25; 560/26; 560/27; 560/28; 560/29;
560/30; 560/31; 560/32; 560/33; 544/282
[58] Field of Search .......... 260/471 C; 560/24, 25-26,
560/27, 28, 29, 30-33

[56] References Cited

U.S. PATENT DOCUMENTS 3,895,054 7/1975 Zajacek et al. .................. 260/471 C

*Primary Examiner*—Vivian Garner
*Attorney, Agent, or Firm*—Fisher, Christen, and Sabol

[57] ABSTRACT

Aromatic urethanes are produced by interacting an aromatic nitro compound, an organic compound containing hydroxyl groups and carbon monoxide in the presence of a catalyst composed of elemental selenium or a selenium compound and of a promoter composed of a bicyclic amidine together with a phenolic compound or a carboxylic acid. The interaction proceeds smoothly with the aid of a small amount of the promoter, attended with secondary production of amino compounds only in small amounts. For instance, 2,4-diethyldicarbamatetoluene is obtained at a yield of 87% by interacting 2,4-dinitrotoluene, ethanol and carbon monoxide in the presence of a catalytic system composed of metallic selenium, 1,8-diazabicyclo(5,4,0)-undecene-7 and acetic acid.

11 Claims, No Drawings

PROCESS FOR PREPARING AROMATIC URETHANES

BACKGROUND OF THE INVENTION

1. Field of the Invention

The present invention relates to a process for preparing aromatic urethanes or aromatic carbamic acid esters. More particularly, this invention relates to a process for synthesizing aromatic urethanes from an aromatic nitro compound, an organic compound having a hydroxyl group and carbon monoxide in the presence of a catalyst.

2. Description of the Prior Art

Aromatic urethanes (hereinafter referred to simply as urethanes) have been heretofore produced generally by reaction of an aromatic isocyanate (hereinafter referred to as isocyanate for brevity) with an organic compound having hydroxyl groups (hereinafter referred to simply as hydroxyl group-containing compound). In recent years, production of isocyanates has become difficult due to shortages and rising costs of starting materials and also due to strong toxicity of intermediate products. Under these circumstances, many novel methods for the production of urethanes have been investigated and developed. However, such methods have not been useful effectively on an industrial scale due to vital defects and problems to be solved.

For example, U.S. Pat. No. 3,338,956 describes a method in which urethanes are produced from an alcohol, carbon monoxide and an aromatic nitro compound (hereinafter referred to simply as nitro compound) in the presence of rhodium chlorocarbonyl as catalyst. In this method, however, the yield of the desired product is low even when the reaction is effected in the presence of a large amount of the catalyst over a long period of time. Therefore, it is not considered that such a method is economically productive of highly pure urethanes.

Further, German Pat. No. 1,543,051 teaches a method for the preparation of urethanes in which a hydroxyl group-containing compound, carbon monoxide and a nitro compound are interacted in the presence of a catalyst of a carbonyl group-containing derivative of a metal of Group VIII of the Periodic Table of Elements in coexistence with a promoter composed of a salt of a metal selected from metals which are capable of existing in two or more valence states. However, this method is not useful on an industrial scale of production since the yield of product is low even when a mononitro compound is employed as starting material, and use of a dinitro compound results in an even lower yield.

Moreover, there has been proposed a method using palladium and a Lewis acid as catalyst (U.S. Pat. No. 3,531,512). By this method, urethanes are obtainable at yields as high as 80%–90% under certain conditions even when a dinitro compound is employed as starting material. In order to attain such high yields, however, the reaction must be effected under severe conditions such as a carbon monoxide initial pressure of 190–350 kg/cm$^2$ and a reaction temperature of 190°–200° C. Additionally, the method has an industrially vital disadvantage in that the Lewis acid, e.g., ferric chloride, used as promoter has a strong corrosive action against metal materials such as iron, stainless steel, etc. Accordingly, it is essential to use a glass or tantalum reactor in order to put this method into practice. The use of a glass or tantalum reactor under the above-described high temperature and pressure conditions presents several technical and economical problems.

Further, there is also known a method using as a catalytic system selenium, sulphur or compounds thereof, and a base or water (French Pat. No. 2,197,862). The reaction conditions of this method are found to be rather mild among the known or proposed methods. The French patent teaches that the bases usable in the method are aliphatic, aromatic and heterocyclic amines, and metal salts of carboxylic acids, sulfonic acids and phosphonic acids. The useful amines are found to be, for example, triethylamine, pyridine, quinoline, N,N-dimethylaniline, diethylamine, tertiary butylamine, 1,4-diazabicyclo(2,2,2)octane, N,N,N',N'-tetramethylethylenediamine, tetramethylenediamine and ethylenediamine. However, in order to satisfactorily induce the reaction in the presence of these amines, it appears necessary to use the amines in a fairly large amount with respect to the starting nitro compound. In fact, when dinitrotoluene is used as the nitro compound, the amine is employed in an amount equal to or greater than that of the dinitrotoluene. Experiments conducted by the present inventors revealed that when the amount of amine was reduced to about 1/6 that of dinitrotoluene, the reaction hardly proceeded, and that, with a reduction to about ⅔, the reaction was considerably slowed down, as will be described in detail in Comparative Examples 2 and 3 hereinafter. The use of such large amounts of amine involves many problems in economy and recovery operations. Further, the method inevitably involves formation of a certain amount of by-products, i.e., amino compounds, even if the reaction conditions are modified to some extent. Accordingly, the yield of urethane is 72%–73% at most. This method is unsuitable for attaining higher yields. As described hereinbefore, the French patent teaches the use of metal salts of carboxylic acids, sulfonic acids, or phosphonic acids as the base. However, the use of these metal salts is considered disadvantageous for the following reason. That is, when potassium acetate, for example, is used as the metal salt, an abnormal exothermic reaction is apt to take place, by which it becomes difficult to properly control the reaction temperature. The raising of the reaction temperature to above 180° C. results in conversion of most of the reaction product to tar-like substances. The yield will be disadvantageously reduced to a considerable extent. In addition, the converted reaction solution emits a strong offensive odor similar to hydrogen sulfide and thus the urethane product obtained from the solution also has such offensive odor. The odor is difficult to remove. According to supplementary experiments conducted by the present inventors, such high yields as indicated in the examples of the French patent specification are difficult to obtain, with amino compounds being secondarily produced in fairly large amounts. Thus, the method of the French patent is not satisfactory for industrial urethane production. There are, accordingly, strong demands for development of more active catalysts and of improvement of yield.

SUMMARY OF THE INVENTION

It is therefore a primary object of the present invention to provide a novel promoter which is usable in a small amount in a process for preparing aromatic urethanes by the use of a selenium catalyst and by which the urethanation reaction can proceed smoothly.

It is another object of the present invention to provide a novel process for preparing aromatic urethanes with reduced amounts of by-produced amino compounds.

It is a further object of the present invention to provide a novel process for preparing aromatic urethanes at high yield.

The above objects can be attained by interacting an aromatic nitro compound, an organic hydroxyl group-containing compound and carbon monoxide in the presence of a catalyst system composed of (1) elemental selenium or a selenium compound and (2) a bicyclic amidine expressed by the general formula:

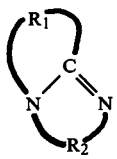

wherein $R_1$ is a linear alkylene group containing from 3 to 6 carbon atoms, $R_2$ is a linear alkylene group containing from 2 to 5 carbon atoms, the alkylene group being non-substituted or substituted with an alkyl group containing from 1 to 4 carbon atoms or a halogen atom, together with a phenolic compound or a carboxylic acid.

DESCRIPTION OF THE PREFERRED EMBODIMENTS

The bicyclic amidines useful in the present invention include, for example, 1,8-diazabicyclo(5,4,0)-undecene-7 (hereinafter referred to as DBU), 1,5-diazabicyclo(4,3,0)-nonene-5 (hereinafter referred to as DBN), and the like. The phenolic compounds to be used in combination with the bicyclic amidine are, for example, phenol, o-, m- and p-cresol, o-, m- and p-xylenol, etc. Phenols having a substitutent such as a halogen, a cyano group or the like which does not impede the urethanation reaction may be also used. Examples of the substituted phenols include halogenated phenols such as o-, m- and p-chlorophenol, o-, m- and p-bromophenol, dichlorophenol etc., cyanophenol and the like. The carboxylic acids employed in combination with the bicyclic amidines include aliphatic carboxylic acids containing from 1 to 6 carbon atoms such as formic acid, acetic acid, propionic acid, oxalic acid, succinic acid, etc., and aromatic carboxylic acids containing from 6 to 12 carbon atoms such as benzoic acid, phthalic acid, hydroxybenzoic acid, etc. The carboxylic acids may be substituted with a halogen atom, a cyano or the like group which does not impede the urethanation reaction of the invention. Examples of the substituted carboxylic acids include monochloroacetic acid, dichloroacetic acid, trichloroacetic acid, trifluoroacetic acid, monochloropropionic acid, cyanoacetic acid, and the like. Further, although sulfonic acids may be employed, the carboxylic acids are more effective.

The bicyclic amidine and the phenolic compound or carboxylic acid may be mixed together to prepare a salt thereof prior to use or may be independently added to the reaction system to be mixed therein. The phenolic compound or carboxylic acid is generally used in an amount of from 0.8 to 1.2 mols, preferably about 1 mol, per mol of the bicyclic amidine. The phenolic compound and the carboxylic acid may be used in combination provided that the above range of the molar ratio to bicyclic amidine is satisfied. Use of the bicyclic amidine alone or the phenolic compound or carboxylic acid alone fails to produce any catalytic activity for the urethanation reaction. Thus, it is essential to use in combination the bicyclic amidine and either the phenolic compound or carboxylic acid for ensuring catalytic activity. As a matter of course, the reaction does not proceed at all when selenium alone is employed without use of the promoter components.

The total amount of either bicyclic amidine and phenolic compound or bicyclic amidine and carboxylic acid is generally 1%–100% by weight, preferably 2%–50% by weight, of the nitro compound. As the promoter is used in greater amount, the reaction proceeds more rapidly. In this sense, the promoter mixture may be used in an amount greater than 100% by weight of the nitro compound. However, it is generally unnecessary to employ such a large amount.

As will be hereinafter illustrated in Comparative Examples 2 and 3, conventionally employed organic amines, e.g., pyridine, triethylamine or the like as described in the French Pat. No. 2,197,862 show substantially no activity when used in small amounts. In addition, use of these amines along with carboxylic acids or sulfonic acids according to the practice of the present invention gives no effect on catalytic activity. Moreover, as described hereinbefore, a bicyclic amidine, phenolic compound or carboxylic acid shows no catalytic effect when used singly. In view of these facts, it seems reasonable to say that the excellent effect of the combination of bicyclic amidine with a phenolic compound or carboxylic acid is inconceivable and unexpected from known preparation techniques.

The catalyst utilizable in the present invention is elemental selenium or a selenium compound. Elemental selenium occurs in several forms such as crystalline selenium, amorphous selenium, vitreous selenium, and the like. In the practice of the invention, elemental selenium of any form can be employed. Selenium compounds usable as catalyst are inorganic and organic selenium compounds including oxides such as selenium dioxide, selenium trioxide, etc., chlorides and sulfides such as selenium oxychloride, selenium disulfide, etc., selenious acid, selenic acid, and both alkali metal and alkaline earth metal salts thereof, selenides such as dimethyl selenide, diethyl selenide, diphenyl selenide, carbonyl selenide, diethyl polyselenide, etc. Of these, elemental selenium or selenium dioxide is preferred.

In order to increase surface area, the elemental selenium or selenium compound may be supported on a suitable carrier such as of carbon, alumina, silica, diatomaceous earth, activated clay, zeolite, Molecular Sieves (synthetic zeolite), barium sulfate, calcium carbonate, ion exchange resins and the like materials. Although the amount of the elemental selenium or selenium compound may vary widely depending on the kind thereof and the reaction conditions, it is generally in the range of 0.1–50% by weight, preferably 1–20% by weight, of the nitro compound when calculated as selenium.

The aromatic nitro compounds used as a principal starting material in the method of the invention include mononitro compounds or polynitro compounds. Suitable mononitro and polynitro compounds include nitrobenzenes, dinitrobenzenes, dinitrotoluenes, dinitronaphthalenes, nitroanthracenes, nitrobiphenyls, bis(nitrophenyl)thioethers, bis(nitrophenyl)sulfons, nitrodiphenoxyalkanes, nitrophenothiazines and heterocyclic compounds such as 5-nitropyrimidine. Typical examples of the nitro compounds include nitrobenzene, o-, m- and p-nitrotoluene, o-nitro-p-xylene, 2-methyl-1-nitronaphthalene, m- and p-dinitrobenzene, 2,4- and 2,6-dinitrotoluene, dinitromesitylene, 4,4'-dinitrobiphenyl, 2,4-dinitrobiphenyl, 4,4'-dinitrobibenzyl, bis(4-nitrophenyl)methane, bis(4-nitrophenyl)ether, bis(2,4-dinitrophenyl)ether, bis(4-nitrophenyl)thioether, bis(4-nitrophenyl)sulfon, bis(4-nitrophenoxy)ethane, α,α'-dinitro-p-xylene, α,α'-dinitro-m-xylene, 2,4,6-trinitrotoluene, o-, m- and p-chloronitrobenzene, 1-chloro-2,4-dinitrobenzene, 1-bromo-4-nitrobenzene, 1-fluoro-2,4-dinitrobenzene, o-, m- and p-nitrophenylcarbamate, o-, m- and p-nitroanisole, 2,4-dinitrophenetole, m-nitrobenzaldehyde, p-nitrobenzoyl chloride, ethyl-p-nitrobenzoate, m-nitrobenzene-sulfonyl chloride, 3-nitrophthalic anhydride, 3,3'-dimethyl-4,4'-dinitrobiphenyl and the like. Isomers and homologues of these aromatic nitro compounds may be also used. These aromatic nitro compounds may be used singly or in combination. Of these, 2,4-dinitrotoluene and 2,6-dinitrotoluene are most preferred when industrial availability of isocyanates is taken into account which are obtained by thermal decomposition of the urethanes produced by the process of the invention.

The hydroxyl group-containing organic compounds suitable for the practice of the invention include monohydric alcohols and polyhydric alcohols containing a primary, secondary or tertiary hydroxyl group. These monohydric or polyhydric alcohols include linear or branched alkyl alcohols containing from 1 to 10 carbon atoms, aralkyl alcohols containing from 1 to 6 carbon atoms in the alkyl moiety, alicyclic alcohols, aryl alcohols, etc. These alcohols may contain a substituent carrying an oxygen, nitrogen or sulphur atom, e.g., a sulfoxide, sulfon, amine, amide, carbonyl or carboxylic acid ester group. Examples of the alcohols are monohydric alcohols such as methyl alcohol, ethyl alcohol, n- and iso-propyl alcohol, n-, iso- and t-butyl alcohol, cyclohexyl alcohol, methylcyclohexyl alcohol, linear and branched amyl alcohol, hexyl alcohol, lauryl alcohol, cetyl alcohol, benzyl alcohol, chlorobenzyl alcohol and methoxybenzyl alcohol, dihydric alcohols such as ethylene glycol, diethylene glycol, propylene glycol, dipropylene glycol and the like, trihydric alcohol such as glycerol, hexantriol and the like. Polyols having greater polyfunctionality may be also employed. Of these, ethyl alcohol is most preferred from an industrial standpoint since the aromatic urethanes obtained by the process of the invention are often subjected to thermal decomposition to obtain isocyanates. The hydroxyl group-containing organic compound is sufficiently used in the theoretical amount, i.e., in an equimolar or greater proportion to the nitro groups of the aromatic nitro compounds. Preferably, an excess of the hydroxyl group-containing organic compound is used.

Although the urethanation reaction of the invention is feasible in the absence of solvent since the hydroxyl group-containing organic compound serves as solvent, a solvent may be used. Examples of the solvent include aromatic compounds such as benzene, toluene, xylene, etc., nitriles such as acetonitrile, benzonitrile, etc., sulfones such as sulfolane, etc., halogenated aliphatic hydrocarbons such as 1,1,2-trichloro-1,2,2-trifluoroethane, etc., halogenated aromatic hydrocarbons such as monochlorobenzene, dichlorobenzene, trichlorobenzene, etc. ketones, esters, tetrahydrofuran, 1,4-dioxane, 1,2-dimethoxyethane and the like.

The order of addition of the starting materials and the catalyst has no restriction and may be arbitrarily changed within limitations of the apparatus employed. For instance, the hydroxyl group-containing compound, the catalyst containing selenium, the promoter composed of a bicyclic diamine and a phenolic compound or a carboxylic acid, and the nitro compound are introduced into a pressure reactor such as an autoclave, into which is further fed carbon monoxide under pressure, followed by agitation under heating conditions until the reaction is completed. The reaction is feasible by intermittently or continuously feeding carbon monoxide while exhausting carbon dioxide which is produced as the reaction proceeds. The reaction may be effected by either a batchwise or a semicontinuous or a continuous manner. Any excess of carbon monoxide remaining in the reaction system after completion of the reaction can be reused by recirculation to the reaction system.

The reaction is generally effected under a carbon monoxide initial pressure of 10–300 kg/cm$^2$G, preferably 20–100 kg/cm$^2$G. The reaction temperature is generally in the range of 80°–220° C., preferably 120°–200° C. The higher reaction temperatures allow the reaction to proceed more rapidly. However, with a reaction temperature above 220° C., thermal decomposition reaction takes place, resulting in reduction in the yield of urethane.

Although the reaction time varies depending on properties of the employed nitro compound, the reaction temperature and pressure, the kind and amount of catalyst and the type of apparatus, it is generally within the range of 5 minutes to 6 hours. After completion of the reaction, the reaction mixture is cooled and gases are exhausted from the system. Then, the reaction solution is treated by a known method such as filtration, distillation or other suitable separation methods for separating the resultant urethane product from unreacted materials, by-products, solvent and catalyst.

The urethane product prepared by the process of the invention has a wide application as starting material for agricultural chemicals, isocyanates or polyurethane.

The present invention will be particularly illustrated by way of the following examples, which should not be construed as limiting thereto the present invention. In the examples, the reactions were effected by the use of an electromagnetic agitation-type stainless steel (SUS 32) autoclave. The conversion and yield were each calculated from the results of a liquid chromatographic analysis and expressed in terms of mol % based on the employed nitro compound.

EXAMPLE 1

12.3 Grams of nitrobenzene, 1.5 grams of DBU, 0.6 gram of acetic acid, 1.0 gram of metallic selenium, and 100 grams of ethanol were introduced into a 500 ml autoclave. The air in the reaction system was replaced first by nitrogen gas and then by carbon monoxide which was fed into the autoclave under pressure until its initial pressure reached 70 kg/cm$^2$G. When agitation was commenced and the temperature was raised to 140° C., reduction in the pressure was observed. The agitation was continued for 60 minutes at 140° C. As a result, no reduction in pressure was observed and thus the reaction was completed. The reaction system was cooled to room temperature and subjected to a gas exhaustion treatment. Then, the reaction system was purged with nitrogen and the reaction product was withdrawn from the purged system. Precipitated selenium was separated from the reaction product and the resultant filtrate was subjected to liquid chromatography revealing that the conversion of nitrobenzene was 100% and the yield of urethane (N-phenylcarbamic acid ethyl ester) was 90%.

EXAMPLE 2

18.2 Grams of 2,4-dinitrotoluene, 1.2 grams of DBU, 0.5 grams of acetic acid, 1.0 gram of metallic selenium and 100 grams of ethanol were used to effect the reaction in the same manner as in Example 1 using an initial pressure of 70 kg/cm$^2$G and a reaction temperature of 160° C. The reaction was completed after 90 minutes. From analytical results of the resultant reaction product, it was revealed that the conversion of dinitrotoluene was 100% and the yield of bisurethane (i.e., 2,4-diethyldicarbamate toluene) was 87%.

EXAMPLES 3-10

Example 2 was repeated using reaction conditions as indicated in the following table, and using, instead of acetic acid, formic acid, oxalic acid, propionic acid, phenol and m-cresol, respectively (Examples 3-7), instead of DBU, DBN (Example 8), instead of 2,4-dinitrotoluene, 2-6-dinitrotoluene (Example 9) and instead of metallic selenium, selenium dioxide (Example 10). The test results are shown in the following table.

was observed even when the temperature was raised up to 200° C.

Further, when the above process was repeated using 1.8 grams of acetic acid along with 3.0 grams of triethylamine, no reaction was induced.

Comparative Example 3

Example 2 was repeated except that 13.2 grams of pyridine was used instead of DBU and acetic acid. No substantial absorption of carbon monoxide was observed at 160° C. When the reaction temperature was raised up to 200° C., slight absorption took place. However, it required 3.5 hours before the reaction was completed.

Comparative Example 4

According to the example described in French Pat. No. 2,197,862, 10.9 grams of 2,4-dinitrotoluene, 65 ml. of ethanol, 0.56 gram of potassium hydroxide, 0.60 gram of acetic acid and 0.5 gram of metallic selenium were used to effect the reaction under an initial pressure of 56 kg/cm$^2$G and a reaction temperature of 160° C. The reaction was completed after 60 minutes. From analytical results of the reaction product, it was revealed that the yield of bisurethane was 47%, 25% of aminocarbamatetoluene and 25% of urea compounds composed of aminocarbamatetoluene component were by-produced.

Table

| | Kind and amount of starting materials and catalytic components | | | | | | | | |
|---|---|---|---|---|---|---|---|---|---|
| Example No. | Nitro compound (g) | | Selenium compound (g) | | Bicyclic amidine (g) | | Organic acid or phenolic compound (g) | | Alcohol (g) |
| 3 | 2,4-DNT[1] | 18.2 | Metallic selenium | 1.0 | DBU[3] | 1.2 | Formic acid | 0.5 | Ethanol 100 |
| 4 | 2,4-DNT | 18.2 | Metallic selenium | 1.0 | DBU | 1.5 | Oxalic acid | 0.5 | Ethanol 100 |
| 5 | 2,4-DNT | 18.2 | Metallic selenium | 1.0 | DBU | 1.5 | Propionic acid | 0.7 | Ethanol 100 |
| 6 | 2,4-DNT | 18.2 | Metallic selenium | 1.0 | DBU | 2.4 | Phenol | 1.5 | Ethanol 100 |
| 7 | 2,4-DNT | 18.2 | Metallic selenium | 1.0 | DBU | 2.4 | m-Cresol | 1.8 | Ethanol 100 |
| 8 | 2,4-DNT | 18.2 | Metallic selenium | 1.0 | DBN[4] | 5.5 | Acetic acid | 2.6 | Ethanol 100 |
| 9 | 2,6-DNT[2] | 18.2 | Metallic selenium | 1.0 | DBU | 1.2 | Acetic acid | 0.5 | Ethanol 100 |
| 10 | 2,4-DNT | 18.2 | Selenium dioxide | 1.5 | DBU | 1.2 | Acetic acid | 0.5 | Ethanol 100 |

| | Reaction Conditions | | | |
|---|---|---|---|---|
| Example No. | Initial Pressure (kg/cm$^2$G) | Temperature (°C.) | Time (min) | Yield of Urethane (%) |
| 3 | 70 | 140 | 120 | 84 |
| 4 | 100 | 150 | 60 | 82 |
| 5 | 70 | 160 | 100 | 80 |
| 6 | 70 | 160 | 100 | 82 |
| 7 | 70 | 160 | 120 | 80 |
| 8 | 70 | 160 | 140 | 85 |
| 9 | 70 | 160 | 120 | 89 |
| 10 | 70 | 140 | 110 | 85 |

1. 2,4-DNT: 2,4-dinitrotoluene.
2. 2,6-DNT: 2,6-dinitrotoluene.
3. DBU: 1,8-diazabicyclo(5,4,0)-undecene-7.
4. DBN: 1,5-diazabicyclo(4,3,0)-nonene-5.

Comparative Example 1

Example 2 was repeated using 2,4-dinitrotoluene, DBU, metallic selenium and ethanol without use of acetic acid. No absorption of carbon monoxide was observed even when the reaction temperature was raised to 220° C. The 2,4-dinitrotoluene remained unreacted and could be recovered.

Comparative Example 2

Example 2 was repeated except that 3.0 grams of triethylamine was used instead of DBU and acetic acid. As a result, almost no absorption of carbon monoxide Another similar reaction was attempted under a reaction temperature of 170° C. However, the reaction system tended to be exothermic and the temperature of the system reached about 200° C. Most of the reaction product was converted to a tar-like substance and only a very small amount of bisurethane was recognized.

What is claimed is:

1. A process for preparing an aromatic urethane comprising interacting an aromatic nitro compound selected from the group consisting of nitro-aromatic hydrocarbons and halogenated nitro-aromatic hydrocarbons, a hydroxyl group-containing organic compound selected from the group consisting of a monohydric alcohol and a polyhydric alcohol and carbon monoxide in the presence of a catalytic system composed of (1) a catalyst selected from the group consisting of elemental selenium and a selenium compound and (2) a promoter composed of a bicyclic amidine having the following general formula:

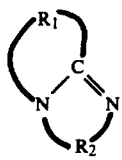

wherein $R_1$ is a linear alkylene group containing 3 to 6 carbon atoms, $R_2$ is a linear alkylene group containing from 2 to 5 carbon atoms, said alkylene group being non-substituted or substituted with an alkyl group containing from 1 to 4 carbon atoms or a halogen atom, and a member selected from the group consisting of a phenolic compound and a carboxylic acid.

2. The process according to claim 1 wherein said aromatic nitro compound is a nitro-aromatic hydrocarbon selected from the group consisting of nitrobenzene, o-, m- and p-nitrotoluene, o-nitro-p-xylene, 2-methyl-1-nitronaphthalene, m- and p-dinitrobenzene, 2,4- and 2,6-dinitrotoluene, 4,4'-dinitrobiphenyl, 2,4-dinitrobiphenyl, bis(4-nitrophenyl)methane, α,α'-dinitro-p-xylene, α,α'-dinitro-m-xylene, 2,4,6-trinitrotoluene and 3,3'-dimethyl-4,4'-dinitrobiphenyl.

3. The process according to claim 1 wherein said hydroxyl group-containing organic compound is ethyl alcohol.

4. The process according to claim 1 wherein said bicyclic amidine is 1,8-diazabicyclo(5,4,0)-undecene-7.

5. The process according to claim 1 wherein said bicyclic amidine is 1,5-diazabicyclo(4,3,0)-nonene-5.

6. The process according to claim 1 wherein said catalyst is selenium.

7. The process according to claim 1 wherein said selenium compound is selenium dioxide.

8. The process according to claim 1 wherein said carboxylic acid is acetic acid.

9. The process according to claim 1 wherein said carboxylic acid is formic acid.

10. The process according to claim 1 wherein said carboxylic acid is oxalic acid.

11. The process of claim 1 wherein said aromatic nitro compound is a halogenated nitro-aromatic hydrocarbon selected from the group consisting of o-, m- and p-chloro-nitrobenzene, 1-chloro-2,4-dinitrobenzene, 1-bromo-4-nitrobenzene and 1-fluoro-2,4-dinitrobenzene.

* * * * *